United States Patent
Koch et al.

(10) Patent No.: US 8,097,751 B2
(45) Date of Patent: Jan. 17, 2012

(54) PROCESS FOR PREPARING POLYISOCYANATES BY THE ADIABATIC PHOSGENATION OF PRIMARY AMINES

(75) Inventors: Daniel Koch, Duisburg (DE); Spotswood Miller, Düsseldorf (DE); Ricardo Serra, Krefeld (DE); Dietmar Wastian, Dormagen (DE); Jürgen Kirsch, Leverkusen (DE); Gerhard Wegener, Mettmann (DE)

(73) Assignee: Bayer MaterialScience AG, Leverkusen (DE)

( * ) Notice: Subject to any disclaimer, the term of this patent is extended or adjusted under 35 U.S.C. 154(b) by 1302 days.

(21) Appl. No.: 11/171,572

(22) Filed: Jun. 30, 2005

(65) Prior Publication Data

US 2006/0025556 A1    Feb. 2, 2006

(30) Foreign Application Priority Data

Jul. 7, 2004    (DE) .................... 10 2004 032 871

(51) Int. Cl.
*C07C 249/00*    (2006.01)
(52) U.S. Cl. ........ 560/347; 560/336; 560/340; 560/359; 560/360; 562/847
(58) Field of Classification Search .......... 560/336, 560/340, 347, 359, 360; 562/847
See application file for complete search history.

(56) References Cited

U.S. PATENT DOCUMENTS

| | | | | |
|---|---|---|---|---|
| 2,908,703 A | * | 10/1959 | Latourette et al. | ............ 560/347 |
| 3,226,410 A | * | 12/1965 | Hettich et al. | ............ 560/347 |
| 3,470,227 A | | 9/1969 | Hatta et al. | |
| 3,544,611 A | * | 12/1970 | Alheritiere et al. | ............ 560/347 |
| 3,947,484 A | * | 3/1976 | Mitrowsky et al. | ............ 560/347 |
| 4,419,295 A | | 12/1983 | Hennig et al. | .......... 260/453 PH |
| 4,549,991 A | * | 10/1985 | Disteldorf et al. | ............ 560/347 |
| 4,581,174 A | | 4/1986 | Ohlinger et al. | ............ 560/347 |

FOREIGN PATENT DOCUMENTS

| | | |
|---|---|---|
| DE | 1 768 439 | 11/1971 |
| DE | 102 22 968 A1 | 12/2003 |
| DE | 102 60 094 A1 | 7/2004 |
| FR | 1126440 | 11/1956 |
| GB | 1341311 | 12/1973 |

OTHER PUBLICATIONS

Ryan, T. Anthony et al, Phosgene and Related Carbonyl Halides, Elsevier, 1996, pp. 277-281.
Abbott, Michael M. et al, Theorie et Applications de la Thermodynamique, McGraw Hill, 1987, p. 9.

* cited by examiner

*Primary Examiner* — Milton I Cano
*Assistant Examiner* — Michael L Leonard
(74) *Attorney, Agent, or Firm* — Lyndanne M. Whalen; Noland J. Cheung

(57) ABSTRACT

A two-stage process for the preparation of organic isocyanates by reacting primary amines with phosgene in which: a) in a first stage, amine and phosgene are reacted in an adiabatically managed reaction, in which the temperature of reaction is restricted to values between 100 and 220° C. by actively adjusting the absolute pressure in the reactor to values between 8 and 50 bar by decompression, and the temperature is held at values between 100 and 220° C. until the stoichiometric conversion of phosgene has reached at least 80%; and then b) in a second stage, the reaction mixture from a) is decompressed to an absolute pressure of 1 to 15 bar and the reaction mixture is reacted further at temperatures between 90 and 240° C., optionally with the introduction of heat.

5 Claims, No Drawings

PROCESS FOR PREPARING POLYISOCYANATES BY THE ADIABATIC PHOSGENATION OF PRIMARY AMINES

This application claims priority under 35 U.S.C. §119 (a)-(d) of German Patent Application No. 1020040328714, filed Jul. 7, 2004.

BACKGROUND OF THE INVENTION

The present invention is directed to a process for preparing a polyisocyanate by reacting the corresponding primary amine with phosgene in an adiabatically managed reaction.

The large-scale preparation of polyisocyanates by reacting amines with phosgene in solvents is well-known and is described in detail in the literature.

DE-A-34 03 204, for example, describes a continuous process for preparing organic polyisocyanates in which an elevated temperature of 100 to 220° C. is used at a pressure of 5-100 bar in a reaction that is performed in a circulated system to some extent.

DE-A-17 68 439 describes a process for the continuous preparation of organic isocyanates in which the amine and phosgene are first preheated and then the preheated constituents are brought together in the reaction zone under high pressure and are reacted under isothermal conditions, i.e. while undergoing heat exchange with the surroundings.

DE-A-102 22 968 describes a process for the continuous preparation of polyisocyanates by reacting primary amines with phosgene in which the reaction is performed in a cascade of temperature-controlled reaction tubes of different sizes.

A common feature of these processes is that, in order to adjust to the desired reaction temperature, temperature-controlled reactors of one form or another (jacket heating, heating via heat-exchangers or special reactor inserts) are unavoidable. However, in particular when synthesizing isocyanates by the phosgenation of amines, external temperature control of the reactors is often a problem because the high temperatures at the walls of the reactor promote or cause the formation of secondary products which then have a negative effect on the yield and/or the properties of the product. In addition, deposits are formed in the reactor which means that the reactors have to be switched off and cleaned at regular intervals. However, this leads to the loss of plant capacity and thus to an economic disadvantage. In addition, the heat transfer units require additional investment costs, which also adversely affect the economic viability of the process.

SUMMARY OF THE INVENTION

The object of the present invention is to provide a simple process for preparing polyisocyanates by the phosgenation of primary amines in which the desired reaction temperature can be set with minimal costs for apparatus and in which at the same time the formation of undesired deposits and secondary products in the reactor can be avoided.

This and other objects which will be apparent to those skilled in the art are accomplished by conducting the process in at least two stages and controlling the reaction temperature and pressure during the first stage of the process to maintain the temperature between 100 and 220° C.

DETAILED DESCRIPTION OF THE INVENTION

The present invention provides a two-stage process for the production of organic isocyanates by reacting primary amines with phosgene in which a) in a first stage, amine and phosgene are reacted in an adiabatically managed reaction, in which the temperature of reaction is restricted to a value between 100 and 220° C. by actively adjusting the absolute pressure in the reactor to a value between 8 and 50 bar by decompression, and the temperature is held at a value between 100 and 220° C. until the stoichiometric conversion of phosgene has reached at least 80%, and then b) in a second stage, the reaction mixture from a) is decompressed to an absolute pressure of from 1 to 15 bar and the reaction mixture is reacted further at a temperature between 90 and 240° C., preferably 90 and 200° C., optionally with the introduction of heat.

The process of the present invention is suitable for the phosgenation of any primary mono- and/or polyamine, in particular for preparing the organic polyisocyanates conventionally used in polyurethane chemistry, such as di- and polyisocyanates of the diphenylmethane series (MDI, PMDI), toluene diisocyanate or naphthalene diisocyanate. Preferred starting materials for the process of the present invention are (a) 3 to 95 wt. % strength, preferably 20 to 75 wt. % strength, solutions of phosgene in suitable solvent(s) and (b) 5 to 95 wt. % strength, preferably 10 to 60 wt. % strength, solutions of mono- or polyamine in suitable solvent(s).

Suitable solvents for preparing the phosgene and amine solutions include any solvents that are inert under the reaction conditions such as, e.g., chlorobenzene, o-dichlorobenzene, dioxane, toluene, xylene, methylene chloride, perchloroethylene, trichlorofluoromethane and/or butyl acetate.

Chlorobenzene or o-dichlorobenzene is preferably used. Obviously, any mixture of the solvents mentioned by way of example may also be used. The same solvent or solvent mixture is expediently used for the amine component and for phosgene, although this is not a strict requirement.

When carrying out the process of the present invention, the phosgene and amine solutions are preferably used in amounts such that the molar ratio of phosgene to primary amine groups in the mixing chamber is from 1.1:1 to 30:1, particularly preferably from 1.5:1 to 5:1.

The reactant solutions may be mixed in accordance with the prior art in static or dynamic mixing units. Static mixing nozzles are preferably used because these can be better insulated against the loss of heat.

The phosgene and amine solutions used may be brought up to a certain temperature before being mixed. The phosgene solution usually has a preferred temperature of from −50° C. to +80° C., more preferably from −20° C. to +70° C. The amine solution may be heated to a preferred temperature of from +25° C. to +160° C., more preferably from +40° C. to +140° C. The temperature of the amine solution is most preferably between +50° C. and +120° C. Setting the temperature of the reactant solutions preferably takes place in a pressurized stage which is performed at a pressure above the vapor pressure of the relevant solution. The phosgene and amine solutions are preferably used at a temperature of from 0° C. to +70° C. and from +80° C. to +120° C., respectively.

An essential feature of the process of the present invention is that the reactor for the reaction of the amine component and phosgene, which are previously combined in a mixing apparatus, is not cooled or heated. Thus, the reactor is not heated or cooled by an external source or sink such as, for example, by a heating or cooling medium or by electrical energy or by any other additional technical agent. In a preferred embodiment of the process, a reactor is used that is insulated against heat exchange with the surroundings so that the first stage in the process in accordance with step a) can proceed in as adiabatic a manner as possible, even under realistic conditions. Insulation may be achieved using a variety of methods that are well-known in the field and may also include the mixing unit.

The residence time made available within the reactor that is required in order to produce the desired conversion is adjusted via the pressure in the reactor. Adjustment of the pressure in the reactor is achieved by controlled decompression. The conversion at this stage of the process according to the invention is sufficient when the consumption of phosgene has achieved 80% of the theoretical (stoichiometric) consumption, preferably 95% of the theoretical consumption, most preferably 99% of the theoretical consumption. According to the invention, the reaction takes place at temperatures of from 100° C. to 220° C., preferably 115° C. to 180° C., particularly preferably at temperatures of 120° C. to 150° C. These temperatures may be set by adjusting the pressure to 8 to 50 bar, preferably 12 to 25 bar. Adjusting the pressure preferably takes place by opening valves mounted on the reactor. On opening these valves, some of the reaction mixture escapes from the reactor. The residence times in the reactor are preferably in the range of from 0.1 to 180 minutes, particularly preferably from 0.5 to 40 minutes, most preferably 1 to 10 minutes.

After mixing the phosgene and amine solutions, there is a rapid rise in temperature in the reactor due to the exothermic production of carbamic acid chloride from phosgene and amine. However, the carbamic acid chloride formed remains largely undecomposed in the first stage under the present pressure and temperature conditions of 8 to 50 bar and 100 to 220° C. respectively, because the solubility of HCl in the reaction mixture is so high, due to the high pressure in the reactor, that the equilibrium for the endothermic carbamic acid decomposition reaction is shifted well towards carbamic acid chloride. Thus the exothermic nature of the reaction forming carbamic acid chloride is sufficient to heat the contents of the reactor to temperatures of from 100 to 220° C. At the same time, due to the lack of external heating in the first stage, there is no localized overheating at the reactor walls or on the surfaces of heat-exchangers, so there is no caking of solids on the walls of the reactor.

The reactor for the first adiabatic stage may have the structural form of any conventional reactor that is suitable for phosgenation reactions. Tubular reactors that are arranged vertically and through which the reactants flow from below are preferred. To keep the residence time distribution narrow, the tubular reactor may be segmented by the use of suitable inserts or baffles. In order to produce production plants with high plant capacity, several tubular reactors may be operated in parallel.

After completing the first stage, in step a), the reaction mixture is decompressed in the second stage, in step b), to a pressure below the pressure in the first stage and a gas phase and a liquid phase containing the isocyanate are withdrawn separately. The pressure in the second stage is 1 to 15 bar, preferably 1 to 7 bar. The temperature and pressure in the second stage are preferably chosen so that less than 90 wt. % of the solvent entering the reactor, more preferably less than 30 wt. % of the solvent entering the reactor, most preferably less than 10 wt. % of the solvent entering the reactor leaves in the gas phase, together with some of the excess phosgene and the HCl formed during the phosgenation reaction. The remaining amount of solvent, the isocyanate and residual amounts of phosgene and HCl are withdrawn from the reactor in the liquid phase.

The second stage, step b), is performed conventionally with the introduction of heat in order to enable the endothermal decomposition of the carbamic acid chloride formed in the first stage, step a). Generally, there are no longer any solids formed during the decomposition of carbamic acid. Therefore it is also safe to externally heat the reactor(s) in the second stage with additional technical agents. Since the second stage is spatially removed from the first adiabatically operated stage, external heating of the reactor(s) in the second stage has no effect on the reaction of phosgene and amine to give carbamic acid chloride in the first stage, step a), which is performed under adiabatic conditions and in which the formation deposition of solids can easily occur, in particular at heated points in the reactor.

The reactor in the second stage may have the structural form of any conventional reactor. The reactor may be heated by a suitable process, e.g. by a heating jacket, by heat-exchangers or by suitable inserts. Tubular reactors with heating jackets are preferred. To produce adequate heat input, vertically arranged shell-and-tube heat-exchangers may also particularly preferably be used as reactors. In order to produce production plants with high plant capacity, several reactors, tubular reactors or shell-and-tube heat-exchangers may be operated, either in parallel or also in series.

After separate separation of the gas phase and the liquid phase from the second reaction stage, the particular mixtures are processed in accordance with the prior art. The gas phase can be divided into the relevant constituents by, e.g., distillation, washing and/or absorption. Phosgene and solvent are preferably recycled to the start of the process. The liquid mixture of substances withdrawn from the second reaction stage is preferably separated into isocyanate(s), solvent, phosgene and hydrogen chloride by rectification. Any traces of carbamic acid chloride still remaining in the isocyanate can be decomposed in a thermal post-treatment stage.

Plants which are operated in accordance with the process according to the invention are characterised by products which are low in secondary products and the absence of deposits in parts of the reactor.

EXAMPLES

Example 1

Comparison Example

A mixture of diphenylmethane diamines and polyphenylene-polymethylene polyamines, so-called PMDA, of the following composition was used for phosgenation:
Concentration of binuclear MDA: 58.4%
Concentration of polynuclear PMDA: >39.2%

27.6 kg/h of a 30 wt. % strength solution of PMDA in chlorobenzene (MCB) with a temperature of about 50° C. and 36.3 kg/h of a 45 wt. % strength solution of phosgene in MCB with a temperature of about 50° C. were mixed continuously in a dynamic mixer (pin mixer). The pressure in the mixer was 7 bar (absolute). At the outlet from the mixer, the reaction mixture had a temperature of 108° C. The rise in temperature in the mixer was caused by the exothermic reaction starting to take place in the mixer.

The reaction mixture was then introduced into an externally heated first tubular reactor with a temperature of 108° C. The pressure in the reactor was 7 bar (absolute). After a reactor residence time of 2 minutes in the first tubular reactor, the reaction mixture, at 140° C., was decompressed to a pressure of 2 bar (absolute) in a second, also heated, tubular reactor.

The residence time in the second tubular reactor was chosen so that the decomposition of carbamic acid chloride was virtually complete.

Phosgene and MCB were removed from the mixture leaving the phosgenation process, in accordance with the prior art, and the mixture was thermally post-treated. The PMDI prepared in this way was characterised by the following product properties:
Concentration of isocyanate groups: 38.1 wt. %
Viscosity at 25° C.: 81 mPas Inspection of the first tubular reactor, operated at 7 bar, performed after the end of the trial revealed clear caking of solids on the internal faces of the tube.

Example 2

According to the Invention

A PMDA with the same composition as that used in Example 1 was used.

17.5 kg/h of a 30 wt. % strength solution of PMDA in chlorobenzene (MCB) with a temperature of about 60° C. and 23.0 kg/h of a 45 wt. % strength solution of phosgene in MCB with a temperature of about 60° C. were mixed continuously in a dynamic mixed (pin mixer). The pressure in the mixer was 22 bar (absolute). At the outlet from the mixer, the reaction mixture had a temperature of 132° C. The rise in temperature in the mixer was caused by the exothermic reaction starting to take place in the mixer.

The reaction mixture was then introduced into a well-insulated first tubular reactor with a temperature of 132° C. The pressure in the reactor was 22 bar (absolute). The reactor was neither heated nor cooled. After a reactor residence time of 2 minutes in the first tubular reactor, the hot reaction mixture was decompressed to a pressure of 2 bar (absolute) in an externally heated second tubular reactor.

The residence time in the isothermally operated second tubular reactor was chosen so that the decomposition of carbamic acid chloride was virtually complete. Phosgene and MCB were removed from the mixture leaving the phosgenation process, in accordance with the prior art, and the mixture was thermally post-treated. The PMDI prepared in this way was characterised by the following product properties:
Concentration of isocyanate groups: 32.0 wt. %
Viscosity at 25° C.: 73 mPas Inspection of the first tubular reactor, operated at 22 bar, performed after the end of the trial revealed no signs whatsoever of the caking of solids on the internal faces of the tube.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A two-stage process for the production of an organic isocyanate by reacting a primary amine with phosgene comprising:
   a) in a first stage, adiabatically reacting the amine and phosgene in a temperature controlled reactor in which reaction temperature is maintained between 100 and 220° C. by actively adjusting absolute pressure in the reactor to values between 8 and 50 bar by decompression until at least 80% of the phosgene has been consumed, and
   b) in a second stage, decompressing reaction mixture from a) to an absolute pressure of 1 to 15 bar and further reacting the decompressed reaction mixture at temperatures between 90 and 200° C., optionally with the introduction of heat.

2. The process of claim 1 in which the reaction temperature in step a) is restricted to between 115 and 180° C.

3. The process of claim 1 in which the absolute pressure in the reactor in step a) is actively restricted to between 12 and 25 bar.

4. The process of claim 1 in which the temperature in step a) is held between 100 and 220° C. until conversion of phosgene has reached at least 95%.

5. The process of claim 1 in which the reaction mixture is decompressed to an absolute pressure of from 1 to 7 bar in step b).

* * * * *